(12) United States Patent  
Richart (10) Patent No.: US 11,370,590 B2  
(45) Date of Patent: Jun. 28, 2022

(54) PACKAGING, PREFERABLY MEDICAL, AND CORRESPONDING ASSEMBLY OF PACKAGINGS

(71) Applicant: SELENIUM MEDICAL, La Rochelle (FR)

(72) Inventor: Olivier Richart, Lagord (FR)

(73) Assignee: SELENIUM MEDICAL, La Rochelle (FR)

( * ) Notice: Subject to any disclaimer, the term of this patent is extended or adjusted under 35 U.S.C. 154(b) by 0 days.

(21) Appl. No.: 15/804,452

(22) Filed: Nov. 6, 2017

(65) Prior Publication Data

US 2018/0178963 A1    Jun. 28, 2018

Related U.S. Application Data

(62) Division of application No. 14/892,059, filed on Nov. 18, 2015.

(51) Int. Cl.
*B65D 75/32* (2006.01)
*A61B 50/30* (2016.01)
(Continued)

(52) U.S. Cl.
CPC .............. *B65D 75/66* (2013.01); *A61B 50/30* (2016.02); *A61F 2/0095* (2013.01);
(Continued)

(58) Field of Classification Search
CPC ........ B65D 75/321; B65D 90/08; B65D 5/32; B65D 5/322; B65D 5/5425;
(Continued)

(56) References Cited

U.S. PATENT DOCUMENTS 593,949 A * 11/1897 Mullins ............... B28B 17/0018  
249/52  
989,086 A     2/1911 Graham  
(Continued)

FOREIGN PATENT DOCUMENTS

CN        201923447        8/2011  
CN        202464396       10/2012  
(Continued)

OTHER PUBLICATIONS

International Search Report dated Jul. 9, 2014.

*Primary Examiner* — Andrew D Perreault  
(74) *Attorney, Agent, or Firm* — Ipsilon USA, LLP (57) ABSTRACT

A packaging element (2, 3) has two shells (21, 22, 31, 32), each shell having a margin (210, 220) defining an access opening giving access to the inside of the shell, said packaging element (2, 3) having at least a "closed" configuration in which the shells form a chamber that is substantially closed and that is suitable for receiving an article, such as a medical implant. The packaging element (2, 3) further has a sealing strip (4) that extends, outside the shells (21, 22, 31, 32), over the entire length of the margins (210, 220) of the shells of the packaging element, and from one margin (210, 220) of the shell to the other margin (220, 210) of the shell in such a manner as to seal the chamber defined by the two shells. An assembly has two packaging elements received one inside the other, with a corresponding sealing method.

18 Claims, 5 Drawing Sheets

(51) Int. Cl.
*A61F 2/00* (2006.01)
*B65D 75/66* (2006.01)
*B65D 43/16* (2006.01)
*A61B 50/00* (2016.01)

(52) U.S. Cl.
CPC .... B65D 43/162 (2013.01); *A61B 2050/0054* (2016.02); *B65D 75/321* (2013.01)

(58) Field of Classification Search
CPC ............ B65D 55/0863; B65D 55/0872; B65D 43/162; A61B 50/30; A61B 19/026; A61B 2050/0054; A61B 2050/3006; A61F 2/0095; B65B 51/10
USPC ... 220/4.01, 686, DIG. 3, 683, 23.87, 23.88, 220/359.1, 359.2, 359.3, 359.4, 359.5, 220/4.21–4.27
See application file for complete search history.

(56) References Cited

U.S. PATENT DOCUMENTS

| | | | |
|---|---|---|---|
| 3,193,129 A | 7/1965 | Pflüger et al. | |
| 3,437,257 A | 4/1969 | Bua | |
| 3,485,408 A | 12/1969 | Benesch | |
| 4,016,806 A | 4/1977 | Schuster | |
| 4,101,031 A | 7/1978 | Cromie | |
| 4,267,940 A | 5/1981 | Wade | |
| 5,069,354 A * | 12/1991 | Tannenbaum | B65D 11/188 190/122 |
| 5,088,611 A * | 2/1992 | Katz | B65D 51/18 215/227 |
| 5,615,770 A | 4/1997 | Applebaum et al. | |
| 8,960,470 B2 | 2/2015 | Tarble | |
| 2003/0214139 A1 | 11/2003 | Nigam | |
| 2008/0019713 A1 | 8/2008 | Volkmann | |
| 2008/0167709 A1 | 10/2008 | Terry | |
| 2010/0140124 A1 | 6/2010 | Hafner | |
| 2012/0285955 A1 | 11/2012 | Tarble | |
| 2015/0231033 A1 * | 8/2015 | Agren | B65D 25/108 206/568 |

FOREIGN PATENT DOCUMENTS

DE 202008009661 10/2008
FR 2656792 7/1991

* cited by examiner

FIG.1

(PRIOR ART)

PACKAGING, PREFERABLY MEDICAL, AND CORRESPONDING ASSEMBLY OF PACKAGINGS

RELATED APPLICATION

This application is a divisional application Ser. No. 14/892,059, filed on Nov. 18, 2015, which is a National Phase Application of PCT/FR2014/051222, filed on May 26, 2014, which in turn claims the benefit of priority from French Patent Application No. 13 54717 filed on May 24, 2013, the entirety of which are incorporated herein by reference.

BACKGROUND

Field of the Invention

The present invention relates generally to packaging elements for packaging articles, and in particular for packaging medical-use parts that are preferably sterilized.

Description of Related Art

Figure 1:
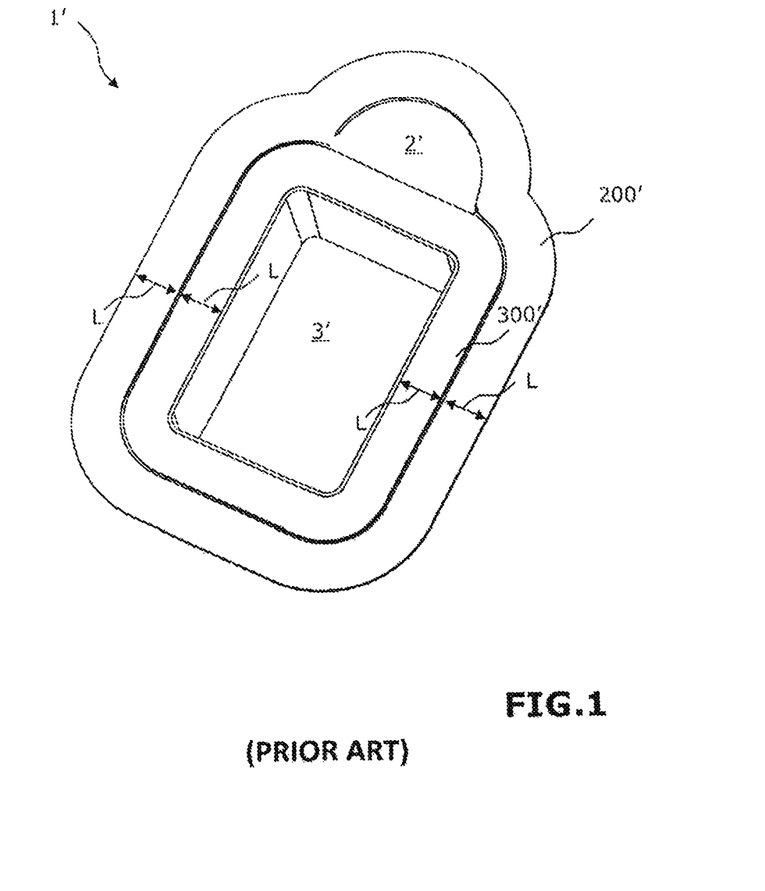
FIG. 1 is a view of an assembly made up of two packaging elements that is known from the state of the art.

As shown in FIG. 1, a medical assembly 1' is known from the state of the art that comprises firstly an "inner" packaging element 3' designed to enclose a part, such as an implant (not shown), and secondly an "outer" packaging element 2' containing the inner packaging element 3'.

Each packaging element is in the form of an open shell having its opening closed off by a peel-off sealing sheet (not shown).

It can be observed, however, that each shell 2', 3' has an outwardly-directed peripheral rim 200', 300' that extends around its opening and that extends perpendicularly to the axis of the opening, i.e. perpendicularly to the axis that is orthogonal to the plane of the opening. It is on that outwardly-directed peripheral rim that the sealing sheet is heat-sealed to seal the packaging element formed by the corresponding shell. In other words, each packaging element is sealed while flat.

In order to comply with Standard NF EN ISO 868 (in particular −5) and with Standard NF ISO 11607 (in particular −1), which requires that the shortest path along which a liquid could cross the sealing zone should be at least 6 millimeters (mm), each of said rims that are designed to be covered by respective sealing sheets must have a width of at least 6 mm so as to provide a peripheral sealing zone that has a width of at least 6 mm so that, for each packaging element, a liquid needs to travel at least 6 mm across the sealing zone in order to escape from or penetrate into the packaging element.

As a result of such a design for each of those packaging elements 2', 3', the overall size of the packaging is very large. The presence of a rim of width L=6 mm for each packaging element increases the overall width of the medical assembly 1 by 2×2×6=24 mm.

OBJECTS AND SUMMARY

An object of the present invention is to propose a novel packaging element and a novel nested packaging assembly of two packaging elements that is of small overall size, while also preserving sealing for each packaging element that complies with Standard EN ISO 11607 (in particular −1) and with Standard NF EN ISO 868 (in particular −5).

To this end, the invention provides a packaging element comprising two shells, each shell having a margin defining an access opening giving access to the inside of the shell, said packaging element having at least a "closed" configuration in which the shells form a chamber that is substantially closed and that is suitable for receiving an article, such as a medical implant, said packaging element being characterized in that it further comprises a sealing strip that extends, outside the shells, over the entire length of the margins of the shells of the packaging element, and from one margin of the shell to the other margin of the shell in such a manner as to seal the chamber defined by the two shells.

Sealing along the opening margins of the shells of the packaging element makes it possible to reduce the overall size of the packaging element while also guaranteeing sealing that is impermeable to liquids and to bacteria and that complies with Standard EN ISO 11607 (in particular −1) and with Standard NF EN ISO 868 (in particular −5). In particular, the design of the packaging element of the invention in the form of two shells defining a chamber between them makes it possible to seal the chamber by sealing that is substantially circular and that extends over a small height of the packaging element.

Unlike the technique known from the state of the art, for obtaining a sealing zone for sealing the shells that has a shortest path of at least 6 mm, it is not necessary to provide an outwardly-directed rim on the shell that extends in a direction orthogonal to the opening axis of the shell over a distance of 6 mm. At least a portion of the sealing zone can be defined between the strip and the shells in the direction of the height of the packaging element.

Preferably, the zone of contact between the sealing strip and the shells acts, optionally together with the zone of contact between the margin of one shell and the margin of the other shell, to form a sealing zone across which the shortest path that a liquid needs to travel in order to cross said sealing zone is not less than 6 mm.

Thus, a portion of the sealing zone can also be formed by the zone of contact of one shell margin with the zone of contact of the other shell margin in such a manner as to co-operate with the sealing strip to define a sealing zone that, in order to be crossed by a liquid requires the liquid to travel at least 6 millimeters across said sealing zone.

It should be observed that the width of the sealing strip thus extends substantially along the height of the packaging element, i.e. parallel to the opening axis of the shells, or optionally at a certain angle of inclination, and not in a direction orthogonal to the opening axis, which would increase the overall size of the packaging element to a considerable extent as explained above.

Such a change in the direction of the sealing strip relative to the state of the art makes it possible to reduce the volume of the packaging element and to make it as close as possible to the volume of its content.

Such a design for each packaging element based on two shells that are sealed together along the entire opening zone of the shells also makes it possible to reduce the area of sealable material that is used while also making the contents visible over a wide angular range, and in particular over 360° about the axis of the packaging element, as well as from above and from below said packaging element.

In accordance with an advantageous characteristic of the invention, the two shells of the packaging element are connected together via a hinge.

The hinge may be an element made in one piece with the two shells. The hinge may also be a separate element that is mounted on the shells. The hinge may also be formed by a flexible strip that is, for example, similar to the sealing strip, and that connects together the margins of the two shells over only a fraction of their peripheries.

Advantageously, the sealing strip is applied via one of its ends over the hinge, extends around the packaging element along the margins of the shells and comes back to be applied over the hinge.

In various embodiments of the packaging element of the invention, the margin of one shell has a shape that interfits with the shape of the margin of the other shell.

Preferably, the margin of each shell is extended on the outside of said shell by a rim that projects, relative to the opening zone of the packaging element defined between the margins of the shells, alongside said shell, and that extends spaced apart from the outside wall of said shell, so as to provide an "insertion" space into which a backing piece can be inserted between said rim and the outside wall of said shell.

Advantageously, it is possible to make provision for the rim of each shell to extend over a height, i.e. over a distance substantially parallel to the axis of the opening of the corresponding shell, of about 6 mm. Preferably, the sealing strip has a width of at least 12 mm so as to cover each rim. These values may be smaller so long as the shortest path across the sealing zone remains not less than 6 mm.

Advantageously, each rim has a substantially plane outside face that is either parallel to the axis of the opening of the corresponding shell or that forms a non-zero angle with the axis of the opening of said shell.

In accordance with an advantageous characteristic of the packaging element of the invention, said packaging element is made of a transparent material.

Advantageously, the sealing strip is applied against the packaging element while hot and under pressure.

In a preferred embodiment, the opening zone of the packaging element, defined between the margins of the shells of said packaging element, is closer to the end-wall of one shell than to the end-wall of the other shell of said packaging element.

In accordance with a particular characteristic of the invention, said packaging element includes a grip zone provided at the end of one of the two shells of said packaging element.

The invention also provides an assembly comprising two packaging elements, one of which is an "outer" packaging element, and the other of which is an "inner" packaging element received in the outer packaging element, said assembly being characterized in that each packaging element is a packaging element as described above.

Preferably, when the shells of each packaging element are in the closed configuration, the axis of the openings of the shells of the inner packaging element is substantially parallel to the axis of the openings of the shells of the outer packaging element, the opening zone of the outer packaging element that is defined between the margins of the shells of said outer packaging element and the corresponding opening zone of the inner packaging element being offset relative to each other along the axis of the openings of the shells of the outer packaging element.

The invention also provides a sealing method for sealing a packaging element as described above, said sealing method being characterized in that it comprises the following steps:

positioning the margins of the shells of the packaging element facing each other, and preferably in contact with each other; and applying the sealing strip over the entire length of the margins of the shells.

Preferably, prior to applying the sealing strip, a backing piece is positioned in the corresponding insertion space of each shell, and then the sealing strip is applied against the outside face of each rim that faces away from the corresponding backing piece.

BRIEF DESCRIPTION OF THE DRAWINGS

The invention can be well understood on reading the following description of embodiments given with reference to the accompanying drawings, in which.

DETAILED DESCRIPTION

With reference to the figures and as stated above, the invention relates to a preferably medical assembly 1 comprising an "outer" packaging element 2 and an "inner" packaging element 3 that is suitable for being received in the outer packaging element 2.

Each packaging element 2, 3 is made up of two open shells 21, 22, 31, 32. In other words, each shell defines a blind cavity. The openings of the shells 21, 22, 31, 32 of each packaging element 2, 3 can be brought together and preferably into abutment one against the other, to define a chamber. The chamber defined in this way by the shells 21, 22 of the outer packaging element 2 make it possible to enclose the inner packaging element 3, the chamber of which that is formed by the corresponding shells 31, 32 makes it possible to enclose a preferably medical article.

In particular, the assembly 1 is designed for the purposes of preserving the sterility of said article and with a view to unpacking the article under aseptic or nearly aseptic conditions. For example, said article may be a solid part, such as a screw for surgery, or any other type of article, and in particular any other type of implant. In addition, said article may be a liquid or a powder. Said article, and preferably the various portions of the packaging element, are sterilized, e.g. by radiation.

In particular, each shell 21, 22, 31, 32 of each packaging element 2, 3 has a margin 210, 220 that defines an access opening giving access to the inside of the shell. The margins of the shells 31 & 32 are not visible in the figures since they are covered over by the sealing strip 4, but the description given of the margins 210, 220 of the shells 21 & 22 also applies to the margins of the shells 31 & 32.

Each packaging element 2, 3 has at least a "closed" configuration in which said access margin of a shell comes to face, and preferably into contact with, the access margin of the other shell to form a substantially closed chamber. Each packaging element 2, 3 also has an "open" configuration in which said chamber is open in such a manner as to make it possible to access the contents of said chamber. To this end, in the non-sealed state, the shells of a packaging element are moveable relative to each other, e.g. by being separated or by hinging, as described in detail below.

Each margin of a shell has a defined width between the inner peripheral outline of the opening of the shell and the outer peripheral outline of the opening of the shell. In other words, the margin has a width corresponding to the thickness of the shell at its mouth. The margin of a shell thus corresponds to the area of the periphery of the mouth of the shell that is suitable for coming to face or into contact with the opposite margin of the other shell.

Each margin stops at the hinge coupling the shells together when such a hinge is present, as described in detail below.

Each shell 21, 22, 31, 32 of a packaging element has an axis A2, A3 orthogonal to the midplane of the opening of the shell and passing substantially through the center of said opening. This axis is referred to as the "axis of the opening" or as the "opening axis" of the shell. When a packaging element is in the closed position, the axis of the opening of one shell of the packaging element substantially coincides with the axis of the opening of the other shell of the packaging element so that it corresponds to the axis of the packaging element or indeed to the axis of the opening zone of the packaging element, i.e. to the axis orthogonal to the midplane extending between the margins of the shells of the packaging element when said packaging element is in the closed configuration.

It is possible to make provision for each packaging element 2, 3 to be made integrally in one piece. Each shell is preferably thermoformed. In a variant, each shell may be made by molding, e.g. by injection molding. Each shell is of a general shape that is circularly symmetrical about the axis of the opening of the shell. Each shell can take other shapes, but such shapes are preferably without any sharp edges at the sealing zone in which the shells are sealed together so as to facilitate proper application of the sealing strip 4 against said opening zone of the shells.

Each packaging element 2, 3 has a sealing strip 4 that extends, outside the shells, over the entire length of the margins 210, 220 of the shells of the packaging element, from one margin of the shell to the other so as to come, via the outsides of the shells, to cover the opening zone of the shells in such a manner as to seal the chamber defined by the two shells. The opening zone of the shells corresponds to the zone defined between said margins of the shells. This opening zone may be formed by an interstitial space or by the zone of contact between the margins, depending on whether or not the margins bear/are in contact one against the other.

Preferably, the sealing strip 4 is a peel-off strip. Once the strip is applied, it can be removed by pulling it to peel it off. "Peel-off" is used to mean that the strip does not tear while it is being removed, while the adhesive remains on the previously sealed zone of the shells.

In a variant, provision may be made for the strip to be a tear-off strip. In an embodiment, said strip is heat-sealable, and, for example, made of a non-woven synthetic material manufactured from polyethylene fibers and usually sold under the registered trademark Tyvek. Provision may be made for this technique of hot-sealing under pressure to be replaced with some other sealing technique, e.g. using a suitable chemical adhesive.

When the sealing strip 4 is a heat-sealable strip, said strip is applied against each packaging element 2, 3 while hot and under pressure. The sealing strip 4 has a face provided with adhesive that becomes active when it is applied against the surfaces to be sealed with a given pressure and at a given temperature.

The sealing strip 4 thus covers the margins, in particular the outer peripheries of the margins of the shells, while extending continuously from one margin of the shell to the other. The sealing strip 4 also extends beyond said margins in a direction corresponding to said width of the strip and substantially parallel to the axis of the opening of each shell. In other words, the strip extends on either side of each opening margin so as to go beyond each margin towards the end-wall of the corresponding shell in order to guarantee good sealing of the packaging element at the margins of the shells, i.e. over the entire length of the space or of the contact zone defined between the margins and over a width greater than said space or than said contact zone.

The sealing strip 4 of a packaging element 2, 3 thus covers the separation zone at which the shells of said packaging element separate and which forms a join plane between the shells. The join plane of the shells of a packaging element corresponds to the midplane extending between the margins of the shells when one margin bears against the other.

The fact that each packaging element is designed in the form of two shells that co-operate to define a chamber makes it necessary to seal only the opening zone of said shells by applying the strip around the packaging element along the margins of the shells, thereby reducing the sealing area used and the overall size of the packaging element, while also offering excellent visibility of the contents of the packaging element when said packaging element is transparent. In particular, the contents of the packaging element are visible over 360° about the axis of the packaging element, and from above and below, i.e. over its entire surface except for the small zone of the surface of the packaging element that is occupied by the sealing strip.

As stated above, when the sealing strip of a packaging element 2, 3 is removed or torn off, said shells of the packaging element can be moved relative to each other into an open position making it possible to access the inside of said packaging element, i.e. the insides of the shells.

Figure 2:
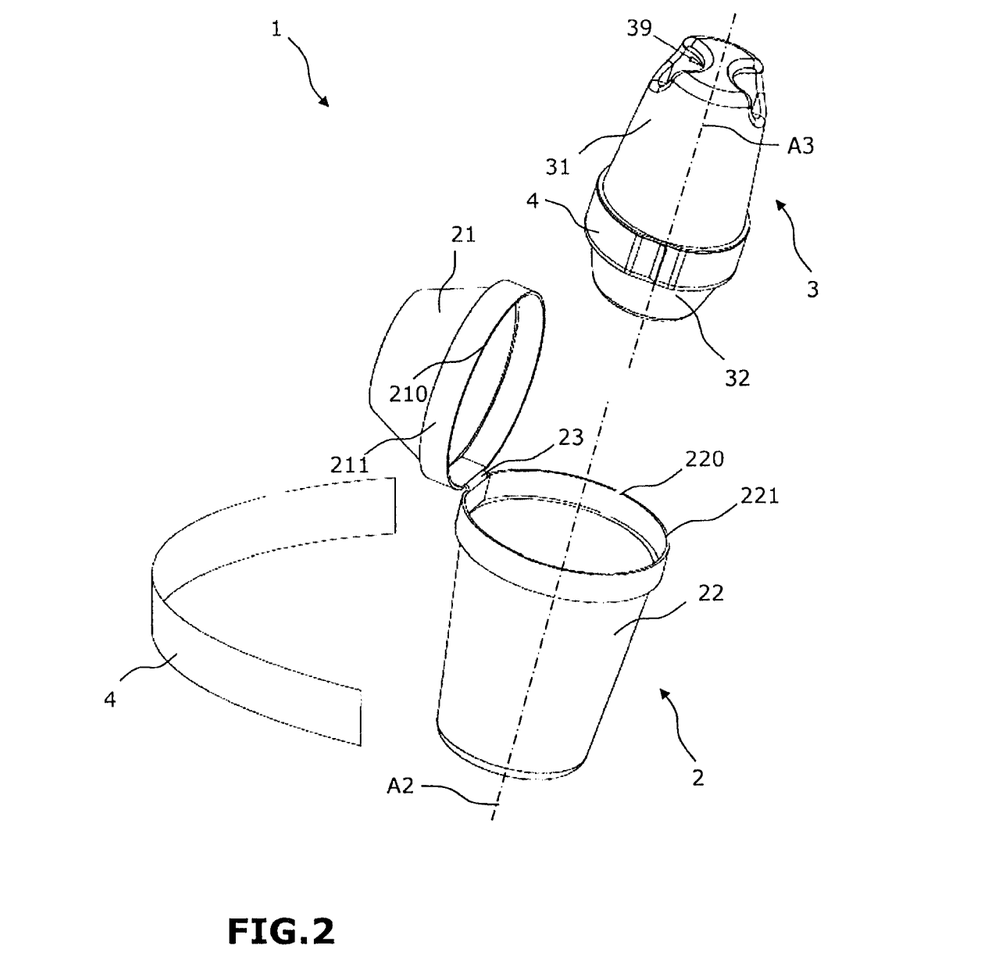
FIG. 2 is a perspective view of an embodiment of an assembly of the invention showing a sealed inner packaging element to be received in an outer packaging element, the shells of which are designed to be sealed together.
Figures 3, 3A:
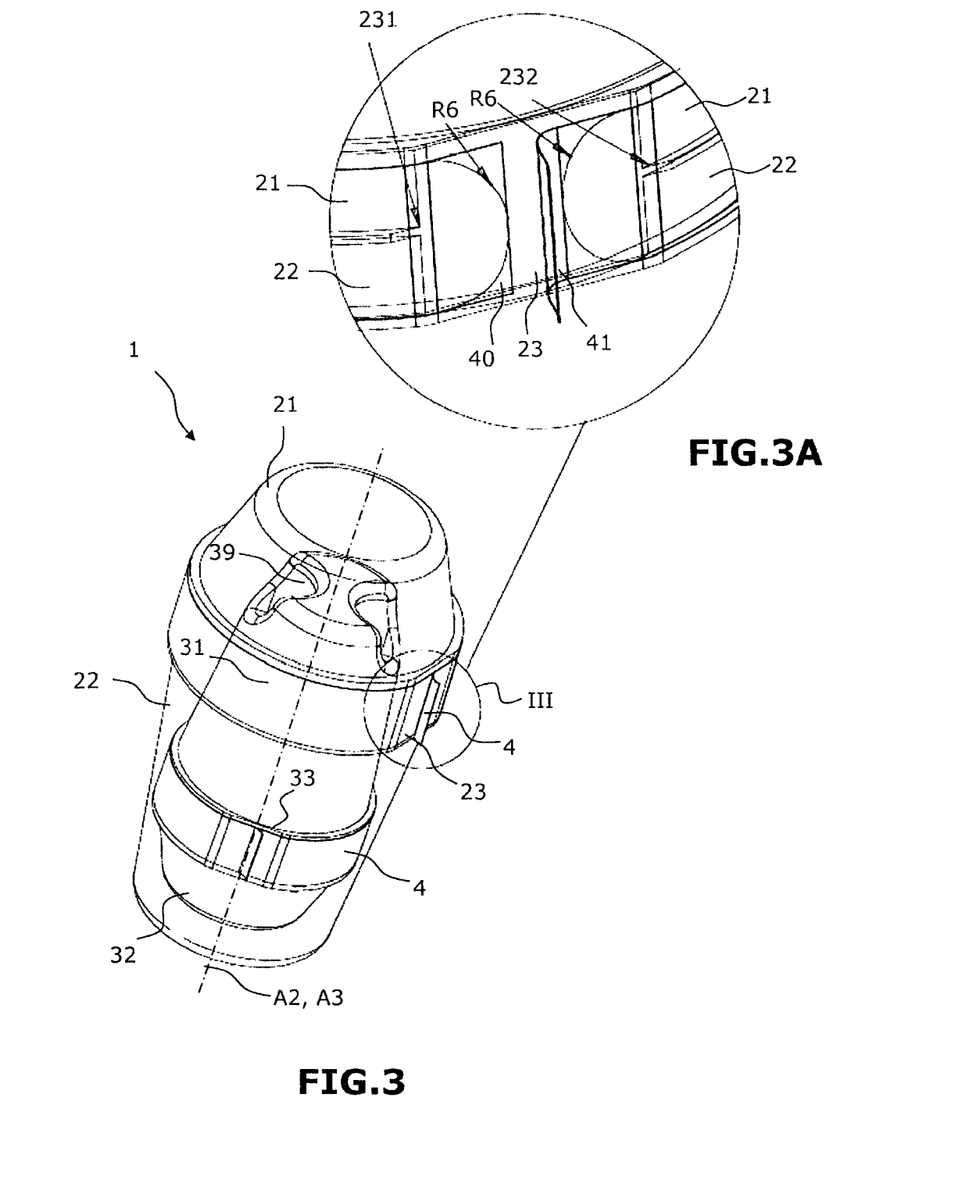
FIG. 3 is a view of the FIG. 2 assembly in the state in which the inner packaging element is inserted inside the outer packaging element and in the state in which said outer packaging element is sealed.
FIG. 3A is a detail view of the zone referenced III of the FIG. 3 assembly.
Figure 4:
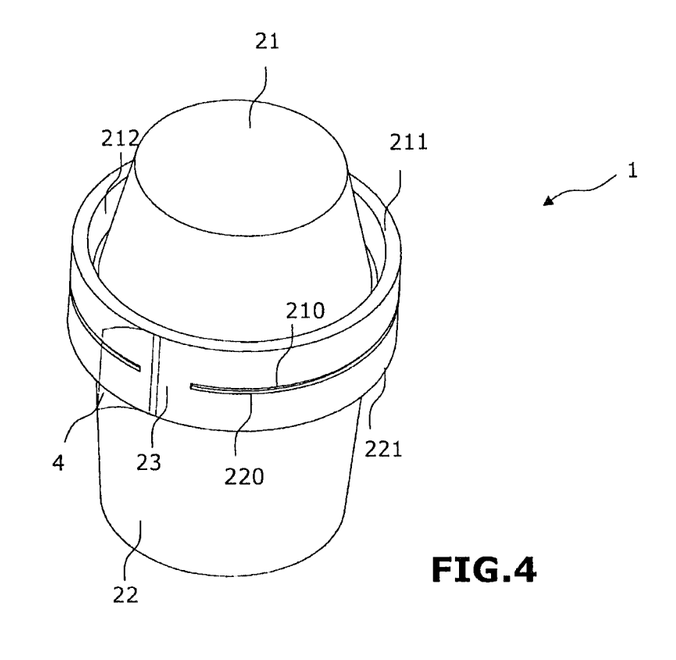
FIG. 4 is a view of a particular embodiment of a packaging element of the invention.

In the example shown in FIGS. 2 and 3, the two shells 21, 22, 31, 32 of each packaging element are connected together via a hinge 23, 33. The ends of said sealing strip 4 at least overlap the hinge zones 23, 33 that are adjacent to the margins 210, 220 of the shells. The zone of overlap of the strip over each hinge portion that is adjacent to the margins of the shells extends over a radius R6 of at least 6 mm so as to comply with Standard NF EN ISO 868 (in particular −5) and with Standard EN ISO 11607 (in particular −1). The length of 6 mm corresponds to the minimum length of barrier that a liquid needs to cross to enter or exit from the packaging via the shortest path, thereby guaranteeing good sealing. The center 231, 232 of the sealing circle of radius R6 associated with each portion of hinge 23 that is covered by the overlapping corresponds substantially to the end 231, 232 of the opening zone of the shells that is situated close to the corresponding hinge portion.

More precisely, as shown more particularly in FIGS. 3 and 3A, the sealing strip 4 is applied over the hinge 23 of the corresponding packaging element 2, e.g. via a first end 40, and is then wrapped around the packaging element along the opening zone of the shells and comes back to be applied over the hinge. The second end 41 of the strip can be applied directly onto the hinge and/or overlap the opposite first end 40 of the strip. The description of how the sealing strip 4 is applied to the outer packaging element 2 is also applicable to the inner packaging element 3.

Very good impermeability to bacteria and to liquid is thus obtained without interruption along the opening zone of the shells. Conversely, if one end of the strip were to overlap its other end at a portion of the opening zone of the packaging element, that might cause poor sealing.

Advantageously, the hinge 23, 33 of a packaging element 2, 3 is formed in one piece with the two shells of the packaging element. In practice, the portion of said hinge that connects the shells together may be formed by a deformable coupling zone, e.g. made of a plastics material. Thus, in the example shown in FIG. 2, the hinge 23 is formed in the wall of each shell 21, 22 of the packaging element 2.

Figure 5:
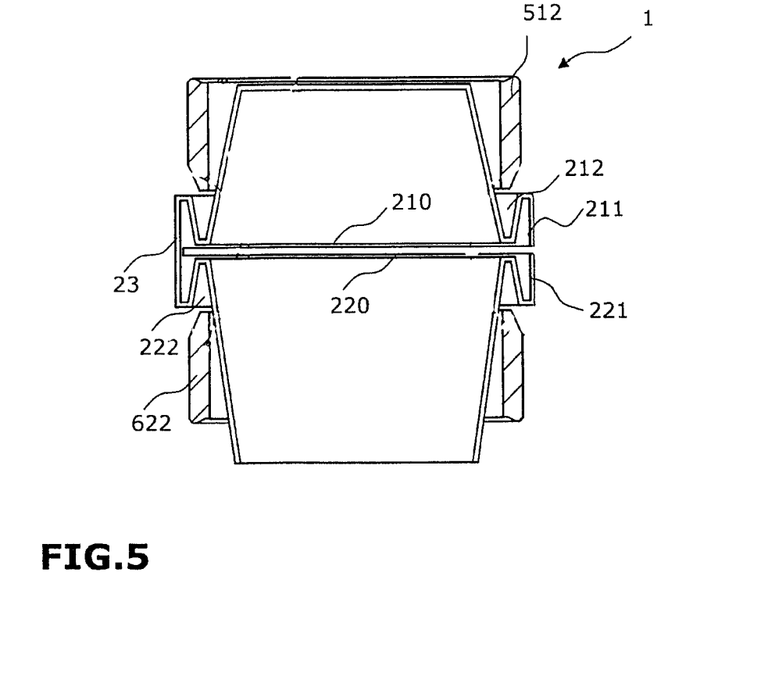
FIG. 5 is a fragmentary axial section view of the FIG. 4 packaging element in the state in which two backing pieces are mounted before the shells are sealed together.

It is also possible, as shown in FIG. 5, to make provision for the hinge 23 to be made in the thickness of the rims 211, 221 (described in detail below) that extend the margins 210, 220 of the shells. In particular, the face of the hinge 23 that faces towards the outside of the packaging element 2 extends in continuity with the outside face of each rim. The rim that extends each margin then projects continuously all the way around the shell, including over the hinge. The hinge that connects the two shells together then extends within the footprint of the rims that extend the margins of the shells.

In a variant, it is possible to make provision for each rim of the shell to extend said margin only, and thus to be interrupted at the hinge between the shells.

Figure 6:
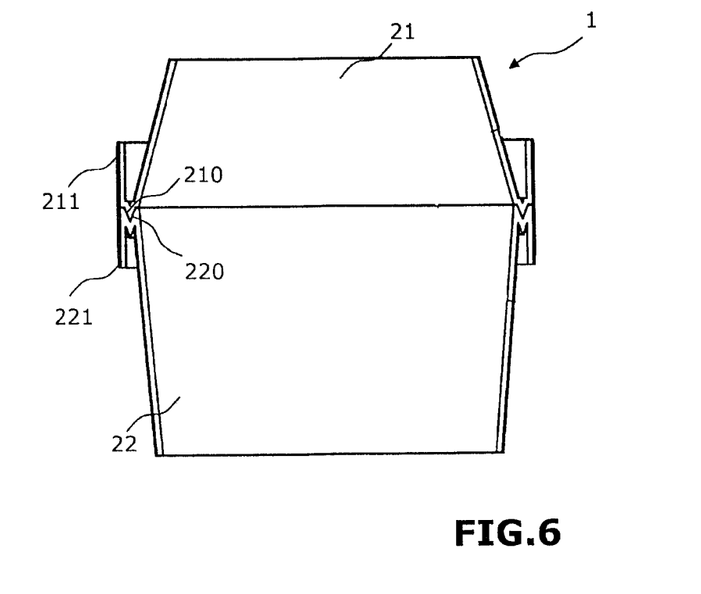
FIG. 6 is a fragmentary view in axial section of another embodiment of a packaging element of the invention.
Figure 7:
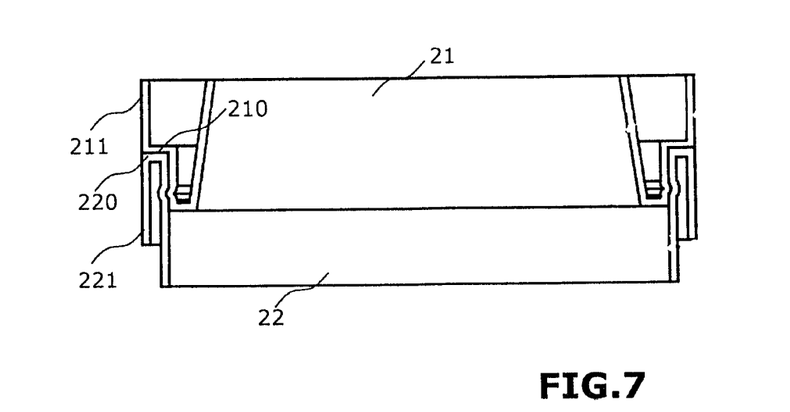
FIG. 7 is a fragmentary view in axial section of another embodiment of a packaging element of the invention.

FIGS. 6 and 7 show embodiments of packaging elements for which the margin 210, 220 of one shell has a shape that interfits with, i.e. that is complementary to the shape of the margin 220, 210 of the other shell. Providing such interfitting shapes makes it possible to improve the sealing and in particular to increase the length of the barrier to be crossed by any liquid.

Each access margin 210, 220 of a shell 21, 22, 31, 32 is extended on the outside of said shell 21, 22, 31,32 by a rim 211, 221. Said rim 211, 221 projects, relative to the opening zone of the packaging element defined by the access margins of the shells, alongside said shell 21, 22, 31, 32, and extends around the shell while being spaced apart from the outside wall of said shell 21, 22, 31, 32, so as to provide an "insertion" space 212 via which a backing piece 512, 622 can be inserted between said rim 211, 221 and the outside wall of said shell 21, 22, 31, 32. The backing piece 512, 622 may be removable or it may remain secured to the packaging element.

In the example shown in the figures, each rim 211, 221 has an outside face that is substantially plane and that is parallel to the axis of the opening of the corresponding shell of the packaging 2, 3. Said outside face of each rim projects substantially circularly around the packaging element.

In a variant, it is possible to make provision for certain rims or the rims to form a non-zero given angle with the axis A2, A3 of the opening of the corresponding shell of the corresponding packaging element 2, 3.

Advantageously, each packaging element 2, 3 is made of a material that is transparent, and preferably of a thermoplastic material or of a molded plastics material, e.g. of an injection-molded plastics material. The transparency of the packaging elements makes it easy to determine the nature of the article contained in the inner packaging element 3.

Like the opening zone defined between the access margins of the shells of the outer packaging element 2, the opening zone of the inner packaging element 3 is closer to the end-wall of one shell than to the end-wall of the other shell of said packaging element.

The offset of the opening zone of each packaging element 2, 3 relative to the center of the packaging element makes it possible to give a preferred direction to the way in which the corresponding packaging element 2, 3 is presented and to the way in which it opens. The large shell 22 can thus be held and/or presented at a height lower than the height of the smaller shell 21. In particular, such a design for each packaging element makes it possible to define, for the user, a lower shell that is designed to form the bottom of the packaging element for retaining its contents when the packaging element is open, and an upper shell forming a lid for closing the packaging element. The opening zone being offset from the center of the packaging element also improves the visibility of the contents of the packaging element.

The inner packaging element 3 is provided with a grip zone 39 adapted to receive at least finger and thumb of one hand. The grip zone 39 is provided at the end of one of the two shells 31, 32 of said inner packaging element 3. The grip zone 39 may have one or more changes in section at the shell, e.g. by the end-wall of a shell being shaped in recessed manner or in projecting manner. In the example shown in FIGS. 2 and 3, the grip zone 39 is provided on the shell 31, which extends projecting from the shell 22 when the outer packaging element 2 is in the open state.

As shown in the figures, the axis A3 of the opening zone of the inner packaging element 3 is substantially parallel to the axis A2 of the opening zone of the outer packaging element 2. The opening zone of the outer packaging element 2 and the opening zone of the inner packaging element 3 are offset relative to each other along the axis A2 of the opening zone of the outer packaging element 2 or indeed along the axis A3 of the opening zone of the inner packaging element 3. Such an offset in the opening zones of the packaging elements 2, 3 makes the article contained in the chamber of the inner packaging element 3 more clearly visible.

For each shell of each packaging element, a preferably annular "backing" or "anvil" piece 512, 622 is provided that is suitable for being inserted into the corresponding space 212, 222 of the shells 21, 22 of the packaging element, so as to come to bear against the peripheral wall of the shell that defines the space between the shell and the wall of the rim 211, 221 that faces towards said peripheral wall of the shell. Thus, the backing pieces 512, 622 inserted into the insertion spaces 212, 222 of each shell of a packaging element make it possible to stiffen the rims of the shells so as to apply the strip 4, while hot and under pressure, against the outside face of each rim, while limiting the risk of the rim and of the corresponding shell being deformed.

Thus, in order to seal one packaging element 2 of nested packaging as described above, firstly the margins of the shells of the packaging element are positioned facing each other, and if possible in contact with each other, in order to seal them together via a strip 4. Preferably, before applying the strip 4, a backing piece 512, 622 is positioned in the insertion space 212, 222 defined between the peripheral wall of each shell 21, 22 and the rim 211, 221 of said shell, and the sealing strip 4 is applied against the outside faces of the rims 211, 221 that face away from the backing pieces 512, 622. The sealing strip 4 is applied while hot and under pressure over the entire length of the margins of the shells. The margins of the shells are then connected together by the same strip 4 that extends along each of the margins and thus from one margin to the other, so that the width of the strip covers the margins of the shells.

The strip may be applied by a movement in relative rotation between the strip and the packaging element, e.g. by applying one or more heated wheels over the strip against the rims of the shells.

The rims of the shells being covered by the strip causes the margins to be covered since the rims extend said margins, the zone of separation between the shells being defined by the margins of the two shells.

In order to unpack the article contained in the assembly 1 and in particular in the inner packaging element 3, it is possible to proceeds as follows.

People working under non-aseptic conditions who might contaminate with their hands the articles they touch can be considered to be "dirty" or "contaminated". Conversely, people working under sufficiently aseptic conditions can be considered to be "clean".

A first person, assumed to be in a contaminated zone, removes the sealing strip 4 from the outer packaging element 2 and moves the shell 21 relative to the shell 22 by pivoting it about the hinge 23 so as to provide access to the inner packaging element 3.

Said "contaminated" first person can thus hold out the inner packaging element 3 without touching it, by holding the outer packaging element 2 by the lower shell 22. Since the inner packaging 3 projects from the shell 22 of the outer packaging 2, it can then be taken hold of by a second person, who is assumed to be in a clean zone. After taking hold of the inner packaging element 3 by the grip zone 39, said clean person can then remove the sealing strip 4 of the inner packaging element 3 so as to open said packaging element by moving the upper shell 32 relative to the lower shell 31 in order to take hold of the article contained in said lower shell 31. Said "clean" person is, for example, a surgeon in an operating theater. The smaller shell 32 is preferably in the upper position so as to form a lid relative to the larger-volume shell 31 that is preferably in the lower position so as to retain the article contained in said inner packaging element 3.

Thus, the article contained in the inner packaging element 3 has never been touched or released while it is being unpacked. In addition, the chamber of the inner packaging element 3 containing the article is opened only once in a clean zone.

The present invention is in no way limited to the embodiments described and shown, and the person skilled in the art can make any variant to them that lies within the spirit of the invention.

The invention claimed is:

1. A packaging element comprising:
a first shell and a second shell, each of said first and second shells having a margin defining an access opening giving access to the inside of said first and second shells, said packaging element having at least a closed configuration in which the first and second shells form a chamber that is substantially closed and that is suitable for receiving an article,
wherein said packaging element further comprises a sealing strip that applies, outside the first and second shells, on the entire length of the margins of the first and second shells of the packaging element, and from the margin of the first shell to the margin of the second shell in such a manner as to seal the chamber defined by the first and second shells,
wherein the margin of the first shell has a shape that interfits with the shape of the margin of the second shell,
wherein the margin of each of the first and second shells is extended on the outside of said first and second shells by a rim that projects, relative to the access opening zone of the packaging element defined between the margins of the shells, alongside said first and second shells, and that extends spaced apart from the outside wall of said first and second shells, so as to provide an insertion space into which a backing piece is insertable between said rim and the outside wall of said first and second shells;
wherein, the sealing strip being applied on and along the rim and the margins of said first and second shells, the packaging element formed by the first and second shells, sealed with the sealing strip, is impermeable to bacteria and to liquid;
wherein the first and second shells of the packaging element are connected together via a hinge;
wherein, the sealing strip having one end that is applied on said hinge, the sealing strip extends around the packaging element and is applied on and along the margins of the first and second shells, and the sealing strip comes back to be applied on the hinge.

2. A packaging element according to claim 1, wherein a zone of contact between the sealing strip and the first and second shells acts, to form a sealing zone across which the shortest path that a liquid needs to travel in order to cross said sealing zone is not less than 6 mm.

3. A packaging element according to claim 1, wherein each rim has a substantially plane outside face that is either parallel to the axis of the access opening of the corresponding first shell or second shell, or that forms a non-zero angle with the axis of the opening of said corresponding first shell or second shell.

4. A packaging element according to claim 1, wherein said packaging element is made of a transparent material.

5. A packaging element according to claim 1, wherein the sealing strip is applied against the packaging element while hot and under pressure.

6. A packaging element according to claim 1, wherein an opening zone of the packaging element, defined between the margins of the first and second shells of said packaging element, is closer to the end-wall of one of the first and second shells than to the end-wall of the other of said first and second shells of said packaging element.

7. A packaging element according to claim 1, wherein said packaging element includes a grip zone provided at the end of one of the first and second shells of said packaging element.

8. An assembly comprising;
two packaging elements, one of which is an outer packaging element, and the other of which is an inner packaging element received in the outer packaging element, wherein each packaging element is a packaging element according to claim 1.

9. An assembly according to claim 8, wherein, when the first and second shells of each packaging element are in the closed configuration, an axis of the access openings of the first and second shells of the inner packaging element is substantially parallel to an axis of the access openings of the first and second shells of the outer packaging element, the access opening zone of the outer packaging element that is defined between the margins of the first and second shells of said outer packaging element and the corresponding opening zone of the inner packaging element being offset relative to each other along the axis of the openings of the first and second shells of the outer packaging element.

10. A sealing method for sealing a packaging element according to claim 1, said sealing method comprising the following steps:
   positioning the margins of the first and second shells of the packaging element facing each other, and preferably in contact with each other; and
   applying the sealing strip over the entire length of the margins of the first and second shells.

11. A sealing method according to claim 10 for a packaging element,
   wherein the margin of each of the first and second shells is extended on the outside of said first and second shells by a rim that projects, relative to the access opening zone of the packaging element defined between the margins of the first and second shells, alongside said first and second shells, and that extends spaced apart from the outside wall of said first and second shells, so as to provide an "insertion" space into which a backing piece can be inserted between said rim and the outside wall of said first and second shells,
   wherein, prior to applying the sealing strip, a backing piece is positioned in the corresponding insertion space of each of the first and second shells, and then the sealing strip is applied against the outside face of each rim that faces away from the corresponding backing piece.

12. A packaging element according to claim 1, wherein a zone of contact between the sealing strip and the first and second shells acts, together with the zone of contact between the margin of the first shell and the margin of the second shell, to form a sealing zone across which the shortest path that a liquid needs to travel in order to cross said sealing zone is not less than 6 mm.

13. A packaging element according to claim 1, wherein the sealing strip is a peel-off strip removable by pulling the sealing strip to peel the sealing strip off so that the sealing strip does not tear while the sealing strip is being removed, while an adhesive of the sealing strip remains on a previously sealed zone of the shells.

14. A packaging element according to claim 1, wherein, the hinge is made in a thickness of the rims that extend the margins of the first and second shells.

15. A packaging element according to claim 1, wherein a face of the hinge that faces towards an outside of the packaging element extends in continuity with an outside face of each rim.

16. A packaging element according to claim 1, wherein, each of said first and second shells is made in one piece and the hinge is formed in one piece with the first and second shells.

17. A packaging element according to claim 1, wherein the sealing strip applies directly from the margin of the first shell to the margin of the second shell.

18. A packaging element according to claim 1, wherein, in said closed configuration in which the first and second shells form a chamber that is substantially closed, the margin of the first shell has a face that is oriented towards a face of the margin of the second shell, and the hinge is formed on said faces of the margins of the first and second shells.

* * * * *